United States Patent [19]

Skinsnes et al.

[11] 3,983,003

[45] Sept. 28, 1976

[54] MYCOBACTERIA CULTURE MEDIUM AND METHOD FOR IN VITRO CULTIVATION OF LEPROSY MYCOBACTERIA EMPLOYING SAME

[76] Inventors: Olaf K. Skinsnes, 438 Portlock Road, Honolulu, Hawaii 96825; Eiichi Matsuo, 3112 Brokaw St., Honolulu, Hawaii 96815

[22] Filed: Jan. 20, 1976

[21] Appl. No.: 650,703

[52] U.S. Cl. ................................ 195/96; 195/100
[51] Int. Cl.² ...................... C12B 3/14; C12B 1/00
[58] Field of Search ............... 195/96, 99, 100, 101, 195/102

[56] References Cited
OTHER PUBLICATIONS

Buchanan et al., *Bergey's Manual of Determinative Bacteriology*, The Williams and Wilkins Company, Baltimore, 8th ed., (1974) pp. 682, 683, 700, 701.

Olitzki et al., "Effect of Inorganic and Organic Substances Containing Sulfur or Nitrogen and of Vitamins on the Growth of Mycobacterium Leprae," *Chemical Abstracts*, vol. 81, No. 13, p. 199 (1974).

Nakamura, "Multiplication of Mycobacterium Lepraemurium in Cell-free Medium," *Chemical Abstracts*, vol. 78, No. 25, pp. 248, 249 (1973).

Dhople et al., "Energetics (adenosine 5'-triphosphate) of Mycobacterium Lepraemurium in Diffusion Chambers Incubated in Vitro and in Mice," *Chemical Abstracts*, vol. 80, No. 13, p. 151 (1974).

*Primary Examiner*—A. Louis Monacell
*Assistant Examiner*—Thomas G. Wiseman
*Attorney, Agent, or Firm*—Holman & Stern

[57] ABSTRACT

A hyaluronic acid-enriched mycobacteria culture medium whose base is either Dubos oleic acid-albumin liquid medium or a physiological mixture of fresh yeast extract in a phosphate buffer of pH 5.5 to 7 optionally containing bovine serum albumin, glycerine, a contaminating organism-growth inhibitory antibiotic, and a gelatinizing agent to solidify the culture medium for plate use. The culture medium has particular utility for the in vitro cultivation of leprosy mycobacteria, which exhibit prolific growth when inoculated and maintained in such culture medium at temperatures within the range of about 25°C to about 37.5°C.

20 Claims, No Drawings

MYCOBACTERIA CULTURE MEDIUM AND METHOD FOR IN VITRO CULTIVATION OF LEPROSY MYCOBACTERIA EMPLOYING SAME

BACKGROUND OF THE INVENTION

This invention relates to the in vitro cultivation of bacilli and, more particularly, to a novel culture medium capable of being employed for the in vitro cultivation of leprosy mycobacteria.

The causative organism of leprosy is an acid-fast rod, *Mycobacterium leprae*, which was first described in 1874 by the Norwegian scientist Armauer Hansen. In the more than a century that has elapsed since Hansen's discovery, many investigators have attempted to grow *M. leprae* in the laboratory for use in leprosy research in testing the effectiveness of proposed new drugs and treatments for leprosy. Although it has been found that rather limited proliferation of *M. leprae*, generally requiring well over a year for any significant growth, will take place on the footpads of mice and inside armadilloes, the previous efforts to cultivate *M. leprae* in vitro have been so unrewarding as to have lead to the designation of this pathogen by many investigators as a mycobacterium which is uncultivable in culture media, probably very fastidious in its growth requirements and quite probably an obligate intracellular parasite. Moreover, the pattern of lesion distribution in leprosy patients has also led to a strongly held hypothesis that the growth of *M. leprae* is low temperature dependent and generally will not occur to any significant degree at physiological temperatures around 37° to 37.5°C.

Recent histochemical studies carried out by the present inventors have led to some novel concepts regarding growth of *M. leprae*, based on findings that concentrations of *M. leprae* in the human host are associated with the presence of acid mucopolysaccharides of the host. Mouse inoculation of *M. leprae* demonstrated that hyaluronic acid applied to the inoculum and inoculation site will promote growth of *M. leprae* in the mouse abdominal wall and peritoneum, neither of which areas have the postulated required low temperature and neither of which support *M. leprae* growth in immunologically intact mice. Extracellular bacilli were abundant and after 1 year of such treatment nerve invasion by bacilli was noted. It was also found that a 0.1% saline solution of hyaluronic acid will support viable bacilli indefinitely in the refrigerator or 37°C incubator but with only minimal proliferation. Based on these findings that hyaluronic acid is a suitable basic growth promoter for *M. leprae* in mice, and presumably is an adequate energy source for *M. leprae*, it was postulated by the present inventors, contrary to the generally held scientific belief established over the last 100 years, that it might be possible to develop a culture medium, enriched with hyaluronic acid, which would be suitable for the in vitro cultivation of *M. leprae*.

SUMMARY OF THE INVENTION

It is, accordingly, a primary object of this invention to provide a method by which leprosy mycobacteria may be successfully cultivated in vitro.

Another object of this invention is to provide a method in accordance with the preceding object, which results in prolific growth of leprosy mycobacteria within relatively short periods of time.

A further object of this invention is to provide a novel mycobacteria culture medium suitable for the in vitro cultivation of leprosy mycobacteria.

Still another object of this invention is to provide a mycobacteria culture medium in accordance with the preceding object, wherein growth of contaminating organisms is inhibited.

A still further object of this invention is to provide a mycobacteria culture medium in accordance with the preceding objects, which may be used either in liquid form or solidified for plate use.

The above and other objects are achieved in accordance with the present invention by providing a hyaluronic acid-enriched mycobacteria culture medium whose base is selected from the group consisting of (a) a physiological mixture comprising fresh yeast extract in an amount of at least about 10% by weight in a phosphate buffer of pH 5.5 to 7 and (b) Dubos oleic acid-albumin liquid medium. The amount of hyaluronic acid present in such culture medium sufficient to promote growth of leprosy mycobacteria is on the order of at least about 0.1% by weight. The fresh yeast extract-containing culture medium base also preferably contains bovine serum albumin, glycerin and an antibiotic in an amount effective to inhibit growth of contaminating organisms, and may be used either in liquid form or solidified for plate use by incorporation of a suitable gelatinizing agent such as agar or agarose.

The above-described mycobacteria culture media may be used in carrying out the in vitro cultivation of a wide variety of mycobacteria, but have been found to be particularly suitable for the in vitro cultivation of the leprosy bacillus, *M. leprae*, as well as the related bacillus, *M. lepraemurium*, which is the causative organism of rodent leprosy. Such in vitro cultivation is carried out in accordance with the present invention by inoculating a viable specimen of the mycobacterium into the culture medium of the present invention, and maintaining the mycobacterium-inoculated culture medium at a temperature within the range of from about 25° to about 37.5°C for a period of time sufficient to grow a culture of the mycobacterium. Under these conditions, prolific growth of *M. leprae* and *M. lepraemurium* has been found to take place in a period of time as short as about 2 weeks.

DESCRIPTION OF PREFERRED EMBODIMENTS

In one of the embodiments of the present invention, the mycobacteria culture medium is a hyaluronic acid-enriched culture medium whose base is a physiological mixture comprising about 70 to 90% by weight of a phosphate buffer of pH 5.5 to 7, about 10 to 20% by weight of fresh yeast extract, 0 to 10% by weight of bovine serum albumin, and 0 to 5% by weight of glycerin. The hyaluronic acid is incorporated in the culture medium in amounts sufficient to promote growth of the mycobacterium to be cultivated therein, which is generally on the order of at least about 0.1% by weight. The culture medium also preferably contains an antibiotic in an amount effective to inhibit growth of contaminating organisms. An antibiotic found particularly suitable for this purpose, for example, is potassium penicillin G, available from Eli Lilly and Co. in the form of a suspension in sodium citrate buffer.

A mycobacteria culture medium of the above type that has been found to be most suitable is one having a base comprising about 76% by weight of a phosphate buffer of pH 6.24, about 15% by weight of fresh yeast extract, about 6% by weight of bovine serum albumin, and about 3% by weight of glycerin, the culture medium being enriched with about 0.1% by weight of hyaluronic acid and further containing potassium penicillin G in an amount of approximately 200 units per milliliter of culture medium base. For carrying out the in vitro cultivation of mycobacteria in accordance with the present invention, this culture medium can either be used as such in liquid form or else be solidified for plate use by incorporation therein of a gelatinizing agent, such as, for example, agar in an amount of 2% by weight or agarose in an amount of about 0.5% by weight.

In formulating the above-described culture medium for the in vitro cultivation of mycobacteria, the pH of the phosphate buffer is of considerable significance, since it should be within the effective pH ranges of the various enzymes which are present in the culture medium and are utilized in the growth of the mycobacteria. For the in vitro cultivation of *M. leprae* and *M. lepraemurium*, a pH within the range of 5.5 to 7 has been found to be suitable, with a pH of 6.24 being optimum.

Although the bovine serum albumin and glycerin are not absolutely essential ingredients in the above culture medium in order for growth of mycobacteria to take place, a more prolific growth will result when these ingredients are present. The bovine serum albumin may be replaced with other sources of albumin, such as, for example, calf serum albumin or goat serum albumin. Likewise, the glycerin may be replaced with various other detergents such as, for example, Tween 80 (a polyoxyalkylene derivative of sorbitan monooleate).

The above-described culture medium may suitably be prepared by forming a first solution by mixing the glycerin and the hyaluronic acid with a portion of the phosphate buffer and autoclaving, for example, at 15 psi for 15 minutes; and forming a second solution by dissolving the bovine serum albumin in the remainder of the phosphate buffer. These two solutions can then be combined, followed by the addition thereto of the fresh yeast extract and the antibiotic. The whole medium can then be filtered, for example, by passing it through a Seitz filter, and thereafter refrigerated until ready for use.

In a second embodiment of the present invention, the mycobacteria culture medium is a hyaluronic acid-enriched culture medium whose base is the standard Dubos oleic acid-albumin liquid medium. This culture medium base, first described by Dubos and Davis in J. Expl. Med., Volume 83, page 409 (1946) contains Tween 80, an oleic acid ester, and albumin (serum fraction V), and is well-known in the art as a culture medium for *M. tuberculosis*, and readily commercially available. This culture medium may be readily prepared for use in accordance with the present invention by dissolving in the Dubos oleic acid-albumin liquid medium a mycobacterium-growth promoting amount of hyaluronic acid, which is generally on the order of at least about 0.1% by weight.

The above-described hyaluronic acid-enriched culture media are capable of supporting growth of the leprosy bacillus, *M. leprae*, as well as the related bacillus, *M. lepraemurium*, at temperatures within the range of from about 25° to about 37.5°C. In carrying out the in vitro cultivation of these mycobacteria in the hyaluronic acid-enriched culture media in accordance with the present invention, a viable specimen of the mycobacterium is first obtained, for example, by harvesting techniques well-known in the art from skin biopsy tissues of patients afflicted with leprosy. The viable specimen of the mycobacterium is then inoculated into the hyaluronic acid-enriched culture medium, and the mycobacterium-inoculated culture medium is then maintained at a temperature within the range of from about 25° to about 37.5°C for a period of time sufficient to grow a culture of the mycobacterium.

Prolific growth of the mycobacteria will take place in the hyaluronic acid-enriched culture media in accordance with the present invention, generally within a period of from about 2 to 6 weeks depending upon such factors as the particular culture medium employed and its form, i.e., liquid or solid, and the conditions of aeration employed. For example, when the cultivation is carried out in an unagitated liquid culture medium in accordance with the present invention, a period of about 6 weeks will generally be required for any significant culture growth to occur. On the other hand, if the liquid culture medium is periodically aerated during the culture growth period by agitation to a surface froth, for example, on a semidaily basis, significant culture growth will take place in about 2 weeks. When the cultivation is carried out as a plate culture on a solid culture medium in accordance with the present invention, for example, one whose base is a phosphate buffer-fresh yeast extract-bovine serum albumin-glycerin mixture solidified for plate use by the incorporation of a gelatinizing agent such as agar or agarose, macroscopic colonies will develope within 2 to 3 weeks.

The invention is further illustrated by way of the following Examples, wherein viable inocula of mycobacteria were obtained from skin biopsy tissues of humans or mice by the following harvesting procedure.

Skin biopsies were obtained in each case under aseptic conditions and kept under refrigeration at 4°C or on wet ice during transport until arrival at the laboratory. This period varied from one day to two weeks. The tissues were then minced and ground in 1/15 M phosphate buffer, pH 6.24. by means of a Potter-Elvehjen homogenizer for 5 to 10 minutes until completely homogenized. After filtering through gauze, the suspension was centrifuged at 1000 rpm (200 g) for 5 minutes, resuspended and centrifuged twice again at 1000 rpm and 2000 rpm (800 g). The final pooled supernatant was then centrifuged at 10,000 rpm (12,000 g at 10°C). Thereafter, the centrifuged residue was treated for 30 minutes at room temperature with mixed equal volumes of 4% NaOH and 2.9% sodium citrate solution for sterilization of possible contaminating micro-organisms. Then the suspension was again centrifuged at 10,000 rpm (10°C), resuspended in 1/15 M phosphate buffer solution and the process repeated three times with the final residue being suspended in a small volume of phosphate buffer or in 0.1% hyaluronic acid in normal saline. Sterile utensils were used throughout, and all procedures, except grinding and centrifugation, were carried out in an ultraviolet light sterilized microbiology hood.

EXAMPLE I

Preparation of culture media a. A liquid culture medium, designated LA-3 medium, was prepared from the following ingredients and amounts thereof:

| | |
|---|---|
| 0.066 M phosphate buffer, pH 6.24 | 81 ml |
| glycerin | 3 ml |
| hyaluronic acid (sodium salt, grade 3-S, from human umbilical cord, Sigma) | 100 mg |
| bovine serum albumin (Cohn Fraction V, Sigma) | 6 gm |
| fresh yeast extract (aseptic Microbiological Associates, Inc., Bethesda, Maryland) | 16 ml |
| potassium penicillin G (Eli Lilly and Co., suspended in factory made sodium citrate buffer 0.6 ml) | 20,000 units. |

In preparing the medium, a first solution was formed by mixing 31 ml of the phosphate buffer, 3 ml of glycerin, and 100 mg of hyaluronic acid, and then autoclaving at 15 psi for 15 minutes. A second solution was formed by dissolving 6 gm of bovine serum albumin in the remaining 50 ml of the phosphate buffer. These two solutions were then mixed together, and to the resulting solution was added 16 ml of fresh yeast extract and 20,000 units of penicillin. The whole medium was then passed through a Seitz filter and refrigerated until ready for use.

b. Solid culture media for plate use, designated LA-3P media, were prepared by incorporating either 2% reagent grade agar or 0.5% agarose into a separate batch of LA-3 liquid medium prepared as above.

c. A liquid culture medium, designated as HA-enriched Dubos medium, was prepared by adding 0.1% by weight of hyaluronic acid to the standard Dubos oleic acid-albumin liquid medium.

d. For purposes of comparison, other culture media were prepared by adding 0.1% by weight of hyaluronic acid to three other standard media (Tarshish, Ogawa, and Wallenstein) normally used for initial growth trials for cultivating acid-fast bacilli.

EXAMPLE II

A viable inoculum of *M. leprae* designated as inoculum A-1, was obtained from a mixture of skin biopsy tissues from two Saigon, five Hong-Kong and two Seoul untreated patients afflicted with type L leprosy. Specimens of inoculum A-1 were utilized for initial growth trials on the three hyaluronic acid-enriched standard media prepared in accordance with Example I(d), above. With each of these three culture media, there was some thin surface growth, particularly with the hyaluronic acid-enriched Tarshish medium, but the cultivated strain was eventually lost by inadequate growth conditions and in contaminants.

Another specimen of inoculum A-1 was inoculated into the abdominal wall of $C_3H$ female mice which subsequently received 0.1% hyaluronic acid intraperitonealy weekly for 1 year. There then was extensive growth of bacilli at the local inoculation site, with nerve invasion, and intraperitoneally. Significant numbers of bacilli were extracellular, suggesting that extracellular growth and proliferation was taking place. These bacilli were harvested from the tissues in the manner described above, to form a secondary inoculum of *M. leprae*, designated as inoculum A-2.

Specimens of inoculum A-2 were inoculated into 4–6 ml quantities of the LA-3 liquid culture medium (Example I(a) above) in capped, 17 × 100 mm glass culture tubes, with the culture tube caps being lose enough to provide some degree of aeration. Half of the tubes were maintained at 25°C, and the other half at 37°C in standard incubators, with no special attention to atmosphere and without any agitation. The cultures were monitored periodically by a combination of the electron-microscopic tellurite viability technique utilizing a Zeiss EM-9$S_2$ instrument, an acid-fast staining technique utilizing Loeffler's methylene blue, and an immuno-fluorescence technique. At both temperatures, the culture growth morphology was basically the same. The bacilli grew relatively slowly, the bacillary forms being initially present as individual or clumped protoplast-like bodies or short rods which are not acid-fast. Gradually, acid-fast forms appeared, and by 6 weeks of cultivation a reasonably heavy precipitate as well as dispersion throughout the medium developed, with the majority of the culture suspension being present as acid-fast rods. The bacillary precipitate was finely granular with a feathery adherence when it was gently shaken up.

The above procedure was repeated with additional specimens of inoculum A-2, but this time the cultures were grown in 50 ml of LA-3 liquid culture medium in 125 ml Erlenmeyer flasks, with aeration being provided by agitation to a surface froth on a semidaily basis. The culture growth was much more rapid than described above, good turbidity with heavy bacillary precipitate developing in 2 weeks, with acid-fast elongate forms predominating.

The above procedures were repeated with additional specimens of inoculum A-2, but this time substituting the HA-enriched Dubos liquid medium (Example I(c), above) for the LA-3 liquid culture medium. The results obtained were similar to those described above for the LA-3 liquid medium.

Additional specimens of inoculum A-2 were inoculated into several samples of the LA-3P solid culture medium (Example I)b), above), and the cultivations were carried out as plate cultures, both at 25° and at 37°C. The growth morphology on the solid medium form rather closely resembles that in the twice-a-day agitated liquid medium. By 24 hours, somewhat vague, colony-like amorphous shapes could be seen with the microscope using a 5x macrotessar lens, a 10x occular and reflected light. By 48 hours, distinct colonies were formative and grayish-white. By 5 days, the colonies were larger, though still microscopic in size, but were beginning to show a brownish-yellow pigmentation. The growth forms at this stage tended to show elongated, non-acid-fast forms with suggestions of some branching, and with portions apparently irregularly acid-fast. By the second to third week, the colonies were clearly macroscopic and became orange-yellow, and consisted of acid-fast rods and long or filamentous shapes. Some of this appearance of elongation was due to end-to-end bacilli in abundance.

EXAMPLE III

A viable inoculum of *M. leprae*, designated as inoculum B-1, was prepared by the above-described harvesting procedure from a mixture of skin biopsy tissues obtained from five Hong-Kong and two Seoul untreated patients afflicted with type L leprosy. A specimen of inoculum B-1 was inoculated on hyaluronic acid-enriched Tarshish solid medium, and the solid medium was coated onto standard glass microslides which had been cut in half longitudinally. These media-slides with inoculated bacilli were inserted into culture tubes containing 0.1% hyaluronic acid in saline and the cultures were thus kept moist and bathed in this solution. A faint surface growth, without distinct colonies developed, but it was noted that a higher concentration of bacilli eventually were found free in the hyaluronic acid-saline solution and it was determined that they could be maintained sometime in this solution and appeared to proliferate slightly in that a fine precipitate of bacilli eventually developed in the bottom of the tube. These findings led to the determination that *M. leprae* can be maintained viably for an indefinite period either by incubation of ice-box storage in the 0.1% hyaluronic acid in normal saline solution, but would not exhibit any significant amount of growth in this medium.

Another specimen of inoculum B-1 was inoculated into the abdominal walls of Swiss female mice which subsequently also received 0.1% hyaluronic acid intraperitoneally at weekly intervals for one year. There then was extensive growth of bacilli at the local inoculation site, with nerve invasion, and intraperitoneally. Significant numbers of bacilli were extracellular, suggesting that extracellular growth and proliferation was taking place. These bacilli were harvested from the tissues in the manner described above, to form a secondary inoculum, designated as inoculum B-2.

Specimens of inoculum B-2 were inoculated into and cultivated in the LA-3 liquid culture medium, the LA-3P solid culture medium, and the HA-enriched Dubos liquid culture medium, in the same manner and under the same conditions as set forth in Example II, above, for the inoculum A-2. Growth of *M. leprae* cultures proceeded in the same manner as described in Example II for the inoculum A-2.

EXAMPLE IV

A viable inoculum of *M. leprae*, designated as inoculum C, was prepared by the harvesting procedure described above from skin biopsy tissues obtained from a 49 year old Hong-Kong male patient afflicted with untreated type L leprosy. Specimens of inoculum C were inoculated into and cultivated in the LA-3 liquid culture medium, the LA-3P solid culture medium, and the HA-enriched Dubos liquid culture medium, in the same manner and under the same conditions as described in Example II, above, for the inoculum A-2. Growth of *M. leprae* cultures proceeded in the same manner as described in Example II for the inoculum A-2.

EXAMPLE V

A viable inoculum of *M. leprae*, designated as inoculum D, was prepared by the harvesting procedure described above from skin biopsy tissues obtained from a 76 year old male Philippine patient, two year Hawaii immigrant, recently untreated, and having relapsed type L leprosy. Specimens of inoculum D were inoculated into and cultivated in the LA-3 liquid culture medium, the LA-3P solid culture medium, and the HA-enriched Dubos liquid culture medium, in the same manner and under the same conditions as described in Example II, above, for the inoculum A-2. Growth of *M. leprae* cultures proceeded in the same manner as described in Example II for the inoculum A-2.

EXAMPLE VI

A viable inoculum of *M. leprae*, designated as inoculum E, was prepared by the harvesting procedure described above from skin biopsy tissues obtained from a 56 year old male Molokai patient having recently relapsed type L leprosy. Specimens of inoculum E were inoculated into and cultivated in the LA-3 liquid culture medium, the LA-3P solid culture medium, and the HA-enriched Dubos liquid culture medium, in the same manner and under the same conditions as described in Example II, above, for the inoculum A-2. Growth of the *M. leprae* cultures proceeded in the same manner as described in Example II for the inoculum A-2.

EXAMPLE VII

A viable inoculum of *M. lepraemurium* (Hawaian strain), designated as inoculum F, was prepared by the harvesting procedure described above from skin biopsy tissues obtained from mice having rodent leprosy. Specimens of inoculum F were inoculated into and cultivated in the LA-3 liquid culture medium, the LA-3P solid culture medium, and the HA-enriched Dubos liquid culture medium, in the same manner and under the same conditions as described in Example II, above, for the inoculum A-2. In all cases, prolific growth of *M. lepraemurium* cultures was obtained.

The mycobacteria culture media of the present invention, as illustrated in the foregoing Examples, find particularly significant utility for the in vitro cultivation of leprosy mycobacteria in that they make it possible for the first time to obtain prolific growth of such mycobacteria in the laboratory in a period of time as short as 2 weeks, thereby reducing to a matter of months the time required to test the effectiveness of proposed new drugs and treatments for leprosy, which previously took years. It is to be understood, however, that the mycobacteria culture media of the present invention have also been found to be useful for the in vitro cultivation of various other mycobacteria, including *M. avium, M. fluorescens, M. fortuitum, M. gordonae, M. kansasii, M. marinum, M. phlei, M. smegmatis, M. xenopi*, and *M. tuberculosis*.

What is claimed is:

1. A culture medium for the in vitro cultivation of mycobacteria comprising a hyaluronic acid-enriched culture medium whose base is selected from the group consisting of (a) a physiological mixture comprising fresh yeast extract in an amount of at least about 10% by weight in a phosphate buffer of pH 5.5 to 7 and (b) Dubos oleic acid-albumin liquid medium, the amount of hyaluronic acid present in said culture medium being at least about 0.1% by weight.

2. The culture medium of claim 1, wherein said culture medium base is Dubos oleic acid-albumin liquid medium.

3. The culture medium of claim 1, wherein said culture medium base is a physiological mixture comprising about 70–90% by weight of a phosphate buffer of pH 5.5 to 7, about 10–20% by weight of fresh yeast extract, 0–10% by weight of bovine serum albumin, and 0–5% by weight of glycerin.

4. The culture medium of claim 3, further containing an antibiotic in an amount effective to inhibit growth of contaminating organisms.

5. The culture medium of claim 3, further containing a gelatinizing agent in an amount effective to solidify said culture medium for plate use.

6. The culture medium of claim 3, wherein said culture medium base is a physiological mixture comprising about 76% by weight of a phosphate buffer of pH 6.24, about 15% by weight of fresh yeast extract, about 6% by weight of bovine serum albumin, and about 3% by weight of glycerin.

7. The culture medium of claim 6, further containing potassium penicillin G in an amount of approximately 200 units per milliliter of said culture medium base.

8. The culture medium of claim 7, further containing agar in an amount of about 2% by weight as a gelatinizing agent to solidity said culture medium for plate use.

9. The culture medium of claim 7, further containing agarose in an amount of about 0.5% by weight as a gelatinizing agent to solidify said culture medium for plate use.

10. A method for the in vitro cultivation of a mycobacterium selected from the group consisting of *Mycobacterium leprae* and *Mycobacterium lepraemurium*, comprising the steps of inoculating a viable specimen of said mycobacterium into a hyaluronic acid-enriched culture medium whose base is selected from the group consisting of (a) a physiological mixture comprising fresh yeast extract in an amount of at least about 10% by weight in a phosphate buffer of pH 5.5 to 7 and (b) Dubos oleic acid-albumin liquid medium, the amount of hyaluronic acid present in said culture medium being sufficient to promote growth of said mycobacterium; and maintaining said mycobacterium-inoculated culture medium at a temperature within the range of from about 25° to about 37.5°C for a period of time sufficient to grow a culture of said mycobacterium.

11. The method of claim 10, wherein the amount of hyaluronic acid present in said culture medium is at least about 0.1% by weight.

12. The method of claim 11, wherein said culture medium base is Dubos oleic acid-albumin liquid medium.

13. The method of claim 11, wherein said culture medium base is a physiological mixture comprising about 70–90% by weight of a phosphate buffer of pH 5.5 to 7, about 10–20% by weight of fresh yeast extract, 0–10% by weight of bovine serum albumin, and 0–5% by weight of glycerin.

14. The method of claim 13, wherein said culture medium also contains an antibiotic in an amount effective to inhibit growth of contaminating organisms.

15. The method of claim 13, wherein said culture medium also contains a gelatinizing agent in an amount effective to solidify said culture medium, and said mycobacterium is cultivated as a plate culture.

16. The method of claim 13, wherein said culture medium base is a physiological mixture comprising about 76% by weight of a phosphate buffer of pH 6.24, about 15% by weight of fresh yeast extract, about 6% by weight of bovine serum albumin, and about 3% by weight of glycerin.

17. The method of claim 16, wherein said culture medium also contains potassium penicillin G in an amount of approximately 200 units per milliliter of said culture medium base.

18. The method of claim 17, wherein said culture medium also contains a gelatinizing agent selected from the group consisting of agar in an amount of about 2% by weight and agarose in an amount of about 0.5% by weight to solidify said culture medium, and said mycobacterium is cultivated as a plate culture.

19. The method of claim 17, wherein said culture medium is in liquid form and is periodically aerated during the culture growth period by agitation to a surface froth.

20. The method of claim 19, wherein said aeration is carried out on a semidaily basis.

* * * * *